United States Patent
Choi et al.

(10) Patent No.: US 6,248,572 B1
(45) Date of Patent: *Jun. 19, 2001

(54) PRODUCTION OF TAXOL FROM TAXUS PLANT CELL CULTURE ADDING SILVER NITRATE

(75) Inventors: Hyung-Kyoon Choi, Taejon (KR); Tom Lee Adams, Millbrae; Roy William Stahlhut, Belmont, both of CA (US); Sang-Ic Kim, Seoul (KR); Jeong-Hwan Yun, Taejon (KR); Bong-Kyu Song, Taejon (KR); Jin-Hyun Kim, Taejon (KR); Jun-Seog Song, Taejon (KR); Seung-Suh Hong, Taejon (KR); Hyun-Soo Lee, Seoul (KR); Ho-Joon Choi, Taejon (KR)

(73) Assignee: Samyang, Genex, Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/218,406

(22) Filed: Dec. 22, 1998

Related U.S. Application Data (63) Continuation-in-part of application No. 08/652,492, filed on May 28, 1996, now Pat. No. 5,871,979.

(30) Foreign Application Priority Data

Apr. 27, 1995 (KR) .................................................. 95-10204

(51) Int. Cl.$^7$ ....................................................... C12P 17/02
(52) U.S. Cl. .......................... 435/123; 435/410; 435/420; 435/422; 435/244; 549/510
(58) Field of Search .................................. 435/123, 244, 435/410, 420, 422; 549/510

(56) References Cited

U.S. PATENT DOCUMENTS

| | | | |
|---|---|---|---|
| 5,407,816 | * | 4/1995 | Bringi .................................... 435/123 |
| 5,637,484 | * | 6/1997 | Yukimune ............................. 435/123 |
| 5,871,979 | * | 6/1997 | Choi ...................................... 435/123 |

* cited by examiner

*Primary Examiner*—Irene Marx
(74) *Attorney, Agent, or Firm*—Darby & Darby (57) ABSTRACT

The present invention provides a method for mass production of taxol which comprises adding sugar into a culture medium containing sugar in the course of semicontinuous culture of Taxus genus plant cell, and a universal method for mass production of taxol which comprises culturing Taxus genus plant cell in a culture medium containing sugar and AgNO$_3$ as well. In accordance with the present invention, large amount of taxol can be produced with a high yield, simply by manipulating the culture condition of Taxus genus plant cell culture.

14 Claims, 8 Drawing Sheets

PRODUCTION OF TAXOL FROM TAXUS PLANT CELL CULTURE ADDING SILVER NITRATE

This application is a continuation-in-part of application Ser. No. 08/652,492, filed May 28, 1996 now U.S. Pat. No. 5,871,979.

FIELD OF THE INVENTION

The present invention relates to a method for mass production of taxol from Taxus genus plant cell culture, more specifically, to a method for mass production of taxol with a high yield by manipulating culture condition for Taxus genus plant cell.

BACKGROUND OF THE INVENTION

Taxanes are diterpene compounds containing a taxane skeleton. For example, taxol is famous as the first identified compound with a taxane ring, which is isolated from the bark of the pacific yew, *Taxus brevifolia* and is effective for the treatment of leukemia and cancer. Recently, it has been reported that: taxol is capable of curing approximately 30%, 50% and 20% of ovarian, breast and lung cancer patients, respectively, by way of inhibiting depolymerization of microtubules (see: E. K. Rowinsky et al., J. Natl. Cancer Inst., 82:1247–1259 (1990)).

To manufacture taxol, total chemical synthesis, semi-synthesis and extraction methods have been employed in the art.

The total chemical synthesis method, however, has not been practically applied in the industry, since it requires very expensive chemical reagents and the yield is not so high, due to the complicated chemical structure of taxol.

The semi-synthetic method employing precursors such as 10-deacetylbaccatin III, has revealed some drawbacks since it essentially entails complicated and multiple steps of isolating and purifying the taxol precursors from Taxus genus plant and transforming the precursors to taxol.

In this regard, the extraction method by which taxol can be isolated from Taxus genus plants in a direct manner, has prevailed in the art, since it has an advantage of economy. However, the said method has revealed a critical shortcoming that it essentially requires a large amount of yew trees to purify taxol, to give rise to the serious environmental disruption.

Accordingly, the ability of total chemical synthesis, semi-synthesis and extraction method to supply taxol for worldwide chemotherapeutic use is not sufficiently assured; and, needs have continued to exist to develop more improved method for taxol production in light of source of taxol.

Under the circumstances, as a promising alternative to solve said problems, a cell culture method has been proposed in the art.

The cell culture-based process, unlike the prior art, has the following advantages: first, taxol can be produced in a steady manner, regardless of fluctuation of supply of yew plants due to the damage by blight and harmful insects, etc.; secondly, cell cultures can be made in large bioreactors, from which taxol can be massively produced by manipulating culture conditions; thirdly, cell cultures produce a simpler spectrum of compounds compared to prior art methods, considerably simplifying separation and purification; fourthly, a cell culture process can adapt quickly to rapid changes in demand; fifthly, a cell culture process can produce taxol as well as taxane precursors such as baccatin that can be converted to taxol.

A variety of methods for producing taxol by utilizing cultured plant cells have been described in the art:

U.S. Pat. No. 5,019,504 discloses a method for producing taxol and its derivative utilizing cultured cells of *Taxus brevifolia*. However, the yield of taxol described therein is 1–3 mg/L, which is insufficient for industrial application. Besides, the production of taxol by the cell culture is unstable, and even when a primary cell of high productivity can be obtained by selection, it is difficult to keep its content by subculturing (see: E. R. M. Wickremesine et al., World Congress on Cell and Tissue Culture (1992)).

U.S. Pat. No. 5,015,744 teaches a semi-synthetic method from baccatain III, which is a precursor in biosynthesis of taxol. By the use of the plant tissue culture, a raw material for the semi-synthetic process such as baccatin III can be produced, thus the plant tissue culture can also be utilized for taxol production by the above-mentioned semi-synthetic process.

WO 93/17121 offers a method for taxol production by cell culture of Taxus genus plant while changing composition of medium, growth rate, and production rate, etc. In case of *Taxus chinensis*, 24.1 mg/L of taxol can be obtained in 18 days of culture and biomass doubles every 2.5 days.

U.S. Pat. No. 5,407,816 describes that *Taxus chinensis* cells are inoculated on a nutrient medium to form a suspension culture and subcultured to a fresh medium to form a producing culture, from which taxol and taxanes can be obtained in a yield of 153 mg/L. The said method was considerably improved in light of taxol productivity, however, it has been proven to be less satisfactory in the sense that it essentially requires so many nutrient media whose compositions are so complicated, and the high productivity can be realized under a rather limited growth condition.

On the other hand, a method for taxol production comprising a step of adding stimulators into culture medium in the course of culturing Taxus genus plant cell to increase productivity of taxol has been suggested in the art. For example, U.S. Pat. No. 5,637,484 discloses an increase of taxol productivity by the addition of jasmonate and Ag-containing compounds into culture medium, where a relatively high concentration (i.e., ~1000 $\mu$M) of complex ion containing Ag is essentially required. However, high level of the Ag-containing compound in the medium plays as an obstacle to normal growth of Taxus genus plant cell, which finally causes low productivity of taxol.

Therefore, there are strong reasons for exploring and developing alternative means for taxol production, which is improved in the senses of productivity and simplicity which are key criteria of a useful method utilized in industrial scale.

SUMMARY OF THE INVENTION

In accordance with the present invention, it has been discovered that: taxol can be simply manufactured with a high productivity, by culturing Taxus genus plant cell in a culture medium containing sugar in a semi-continous manner or by culturing Taxus genus plant cell in a culture medium containing both sugar and $AgNO_3$.

A primary object of the present invention is, therefore, to provide a method for mass production of taxol which comprises adding sugar into a culture medium in the course of semi-continuous culture of Taxus genus plant cell.

The other object of the invention is to provide a method for mass production of taxol which comprises culturing Taxus genus plant cell in a culture medium containing sugar and $AgNO_3$.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

The present inventors first developed taxol-producing cell lines, and compared them with those known in the art. From the comparative studies on the morphological, physiological and growth condition of the taxol-producing cell lines, it has been determined that some of the cell lines are novel ones which are distinguished from those of prior art, in light of taxol productiivity, mode of taxol secretion, etc. Accordingly, one of the preferred cell lines was named *Taxus chinensis* SYG-1 (hereinafter, referred to as "SYG-1" for convenience) and deposited with an International Depositary Authority (IDA), the Korean Collection for Type Cultures (KCTC, Oeun-dong, Yusong-gu, Taejon, Korea) on Mar. 14, 1996, under an accession number of KCTC 0232BP.

All of the prior art describe methods for mass production of taxol by employing batch culture; and, there is no teaching in said patents on, nor is there anticipated, semi-continuous culture of taxol-producing cell lines. In this regard, the inventors first made an effort to develop a novel method for mass production of taxol by way of semi-continuous culture technique.

In accordance with the present invention, taxol can be prepared with a high yield, by adding sugar into culture medium in the course of semi-continuous culture of Taxus genus plant cells, which comprises the steps of:

(i) inoculating Taxus genus plant cells on a culture medium containing 1 to 10% (w/v) sugar, and incubating said cells;

(ii) transferring a part of the culture solution containing the Taxus genus plant cells obtained in step (i) to a fresh medium for a volume ratio of said culture solution to said fresh medium to be in the range of 1/10 to 1/2 and repeating the incubation step (i);

(iii) adding sugar to the solution remaining after transfer of the solution from step (ii) at a concentration of 1 to 10% (w/v) and incubating said cells; and, (iv) recovering taxol from the culture solution in which said taxol is produced by said cells.

After 5 to 30 days of incubation at the step (i), a part of total culture solution is transferred to the other flask containing fresh medium whose contents are the same as the one employed at the beginning of the culture or its equivalents, so that the volume ratio of said culture solution to said fresh medium can be in the range of 1/10 to 1/2, and starts a cycle of culture. Then, the culture solution remaining after the transfer was added 1 to 10% (w/v), more preferably 1 to 5% (w/v) of sugar, and incubated for 30 to 60 days in which taxol production is maximized, where incubation was carried out at 24° C., and an agitation speed of 150 rpm under a dark condition.

On the other hand, $AgNO_3$ may be added to the medium at a concentration of 1 to 15 $\mu$M, more preferably 5 to 10 $\mu$M at day 0 of the semi-continous cell culture process, in order to improve the taxol productivity.

The present invention also provides a method for mass production of taxol with a high yield, which can be applicable for various types of culture including continuous culture, semi-continuous culture, batch culture, fed-batch culture, etc., which comprises the steps of:

(i) inoculating Taxus genus plant cells on a culture medium containing 1 to 10% (w/v) sugar and 1 to 15 $\mu$M $AgNO_3$, and incubating said cells; and, (ii) recovering taxol from the culture solution in which said taxol is produced by said cells.

In carrying out the said methods of the present invention, at the beginning of culture, Taxus geneus plant cells are inocualted on a culture medium containing, most preferably, 4 to 9% (w/v) sugar in a ratio of 4 to 8 g (dry weight) per liter of medium, which may reduce the time required for sufficient taxol production and prevent contamination during culture as a result of rapid cell growth. In this connection, the sugar contained in the culture medium may be one or two selected from the group consisting of glucose, fructose, sucrose and maltose.

On the other hand, Taxus genus plant employed in the methods includes *Taxus brevifolia, Taxus canadensis, Taxus cuspidata, Taxus baccata, Taxus alobosa, Taxus floridana, Taxus wallichiana, Taxus media* and *Taxus chinensis*, though *Taxus chinensis* SYG-1(KCTC 0232BP) which is newly developed by the inventors, is most preferably employed therein.

Further, $NH_4$-citrate and sugar may be added to the culture solution after 5 to 20 days, more preferably 5 to 10 days of incubation at step (i) of the methods, at a concentration of 1 to 15 mM, more preferably 1 to 10 mM, and 1 to 10% (w/v), more preferably 1 to 5% (w/v), respectively.

Quantitative Analysis of Taxol

Taxol which is produced from the culture of *Taxus chinensis* SYG-1 is quantitatively assayed by employing high performance liquid chromatography (HPLC) under a specific condition described in Table 1 below.

TABLE 1

| Condition for quantitative assay of taxol | |
|---|---|
| Instrument | HPLC (Waters, U.S.A.) |
| Column | Capcell Pack $C_{18}$ UG 120 |
| | (length: 250 mm, inner diameter: 4.6 mm) |
| Column temp. | 40° C. |
| Mobile phase | $CH_3CN$: water (20~100% gradient) |
| Fluid speed | 1.0 ml/min |
| Injection volume | 10 $\mu$l |
| Detector | UV(227 nm), ATTE = 3 |

From the quantitative analysis of taxol, it was determined that the taxol productivity of the level of ~300 mg/L is observed in the present invention, when *Taxus chinensis* SYG-1 is incubated for 42 to 49 days by the semi-continuous culture with the addition of $AgNO_3$, $NH_4$-citrate and sugar.

The present invention is further illustrated in the following examples, which should not be taken to limit the scope of the invention.

EXAMPLE 1
Induction and Characterization of Callus From Taxus Genus Plants

The taxol-producing cell lines were isolated from *Taxus chinensis* and *Taxus baccata* by way of callus induction. When plant tissue was incubated on a proper medium containing a hormone, undifferentiated cell of callus was induced: Tissues from bark, needles, stems and roots of *Taxus chinensis* and *Taxus baccata* were washed with tap water and sterilized with Ca-hypochloride solution for 20 to 30 min. Then, the sterilized tissue was washed with distilled water 2 to 3 times, chopped to have a length of 1 cm, and transferred to B5 medium (see: Gamborg et al., Can. J. Biochem., 46:417–421(1968)) supplemented with 20 $\mu$M NAA(naphthoxyacetic acid), 0.4 $\mu$M BAP(6-benzylaminopurine), 1 g/L casein hydrolysate and 30 g/L sucrose (hereinafter referred to as "B5 medium") after solidifying with 0.2% (w/w) gelite, and incubated at a temperature of 24 to 26° C. for 2 to 6 weeks under a dark condition to induce the callus of interest.

The growth medium for callus was selected by observing the growth pattern of the callus with naked eye after transferring the callus to several media well known in the art, e.g., MS (see: Murashige, T. and F. Skoog, F., Physiol. Plant, 5:473(1962)), SH (see: Schenk and Hilderbrandt, Can. J. Bot., 50:199–204(1972)), WPM (see: Lloyd and Mccown, Int. Plant Prop. Soc. Proc., 30:421–427(1981)) and B5 media (see: supra), respectively, and it was determined that the callus showed good growth on the B5 medium.

Then, studies on the morphology, physiology and growth condition were made for the cell lines thus induced, and compared with those of known in the art. As a result, it was determined that: three kinds of *Taxus chinensis* cell lines (i.e., *Taxus chinensis* SYG-1, *Taxus chinensis* HU-1 and *Taxus chinensis* Mairei) and one kind of *Taxus baccata* cell line have a distinction over those of prior art, in light of taxol productivity, mode of taxol secretion, etc. In particular, a *Taxus chinensis* cell line named '*Taxus chinensis* SYG-1' was found to have a novel physiological characteristics and superior taxol productivity among them, which are summarized in Tables 2 and 3 below. In this regard, the *Taxus chinensis* SYG-1 cell line ("SYG-1") was deposited with an International Depository Authority (IDA), the Korean Collection for Type Cultures (KCTC, Oeun-dong, Yusong-gu, Taejon, Korea) on Mar. 14, 1996, under an accession number of KCTC 0232BP.

TABLE 2

Morphology and growth condition of *Taxus chinensis* SYG-1

| *Taxus chinensis* SYG-1 | Characteristics |
|---|---|
| Size | 50–150 $\mu$m |
| Mobility | (−) |
| Agglutination | Weak |
| Aggregation | (+) |
| Adaptation to shear stress | Strong |
| Color of culture | Weak brown |
| Color Temperature | 24° C. |

TABLE 3

Comparison of characteristics of cell lines of the invention and prior art

| Characteristics | SYG-1 | USP 5407816 | USP 5019504 | WO 92/13961 |
|---|---|---|---|---|
| Secretion mode of taxol | intracellular | extra-cellular | not clear | not clear |
| Light-requirement | dark | light | dark | dark |
| Taxol productivity | ~300 mg/L | 153 mg/L | 1–3 mg/L | 0.04% DCW |

EXAMPLE 2
Suspension Culture of SYG-1

To select the most preferred medium for the suspension culture of SYG-1, the cell line was trasferred to MS, SH, WPM and B5 media, respectively, and the growth pattern was observed analogously as in Example 1, which resulted that SYG-1 cell was well grown on B5 medium like its callus. In addition, it was also determined that SYG-1 cell was well grown at a temperature of 24° C., at an agitation speed of 150 rpm.

A serial cultivation of the callus was made every 4 weeks in a case of solidified medium, while transferring a part of tissue by the aid of forceps: A piece of the callus was maintained on the plate of solid medium. Then, the callus maintained on the solid medium was inoculated on a small volume of B5 medium, and small amounts of medium were supplemented to the culture, as the cells grew to increase total volume of culture. Then, well grown cell cultures were diluted in the B5 medium contained in 500 ml Erlenmeyer flask at a ratio of 1/5 (v/v), and subcultured into new suspension culture medium every two weeks.

EXAMPLE 3
Effect of $AgNO_3$ on the Taxol Productivity

It has been well known that $AgNO_3$ is an antagonist of the plant hormone, ethylene, which effects on the plant cell growth and secondary metabolite production. Accordingly, the present inventors tested the effect of $AgNO_3$ on the taxol production in a suspension culture of various kinds of Taxus genus plant cells.

Figure 1:
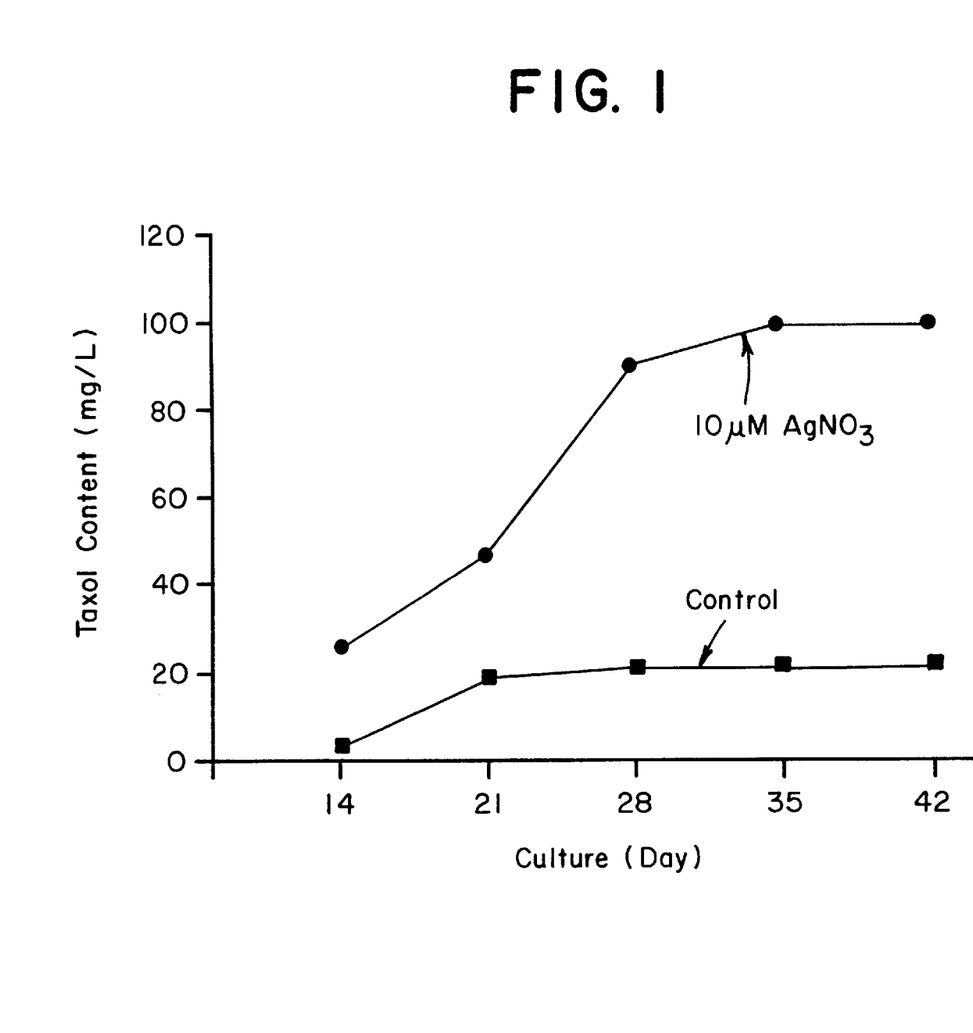
FIG. 1 is a graph showing the effect of $AgNO_3$ on the taxol productivity.

To a 250 ml of Erlenmeyer flask was poured 75 ml of B5 medium containing 10 $\mu$M $AgNO_3$, and 14 day old cell culture was inoculated on this medium in a ratio of ~4 g (dry weight) per liter of medium and incubated in an analogous manner as described in Example 2. Then, the productivity of taxol was compared with a control which did not contain $AgNO_3$(see: FIG. 1). As can be seen in FIG. 1, it was clearly determined that the amount of taxol produced was 98.95 mg/L when $AgNO_3$ was added to a medium (-●-), which is 4.7 times of the control (-○-).

Further, the other *Taxus chinensis* cell lines named *Taxus chinensis* HU-1("HU-1") and *Taxus chinensis* Mairei ("Mairei"), and a *Taxus baccata* cell line, all of which were induced from Example 1, were cultured under the same growth condition as described above. And then, taxol productivities depending on culture period were determined and summarized in Table 4 below.

TABLE 4

The effect of AgNO₃ on taxol productivity in various kinds of Taxus genus plant cells (unit: mg/L)

| Taxus species | Cell line | Day | Control | AgNO₃-treated |
|---|---|---|---|---|
| Taxus chinensis | HU-1 | d21 | ND | 5.7 |
| | | d42 | ND | 8.7 |
| | Mairei | d14 | 0.3 | 20.8 |
| | | d21 | 0.4 | 32 |
| | | d28 | 0.6 | 34.5 |
| | | d35 | 0.3 | 45.2 |
| | | d42 | 0.6 | 53.2 |
| Taxus baccata | | d14 | ND | ND |
| | | d21 | ND | 4.4 |
| | | d28 | ND | 6.4 |
| | | d35 | ND | 5.5 |
| | | d42 | ND | 5.8 |

From the above results, it was found that addition of AgNO₃ increased taxol productivity in all of the tested cell lines.

EXAMPLE 4
Effect of AgNO₃ Concentration on the Taxol Productivity

Figure 2:
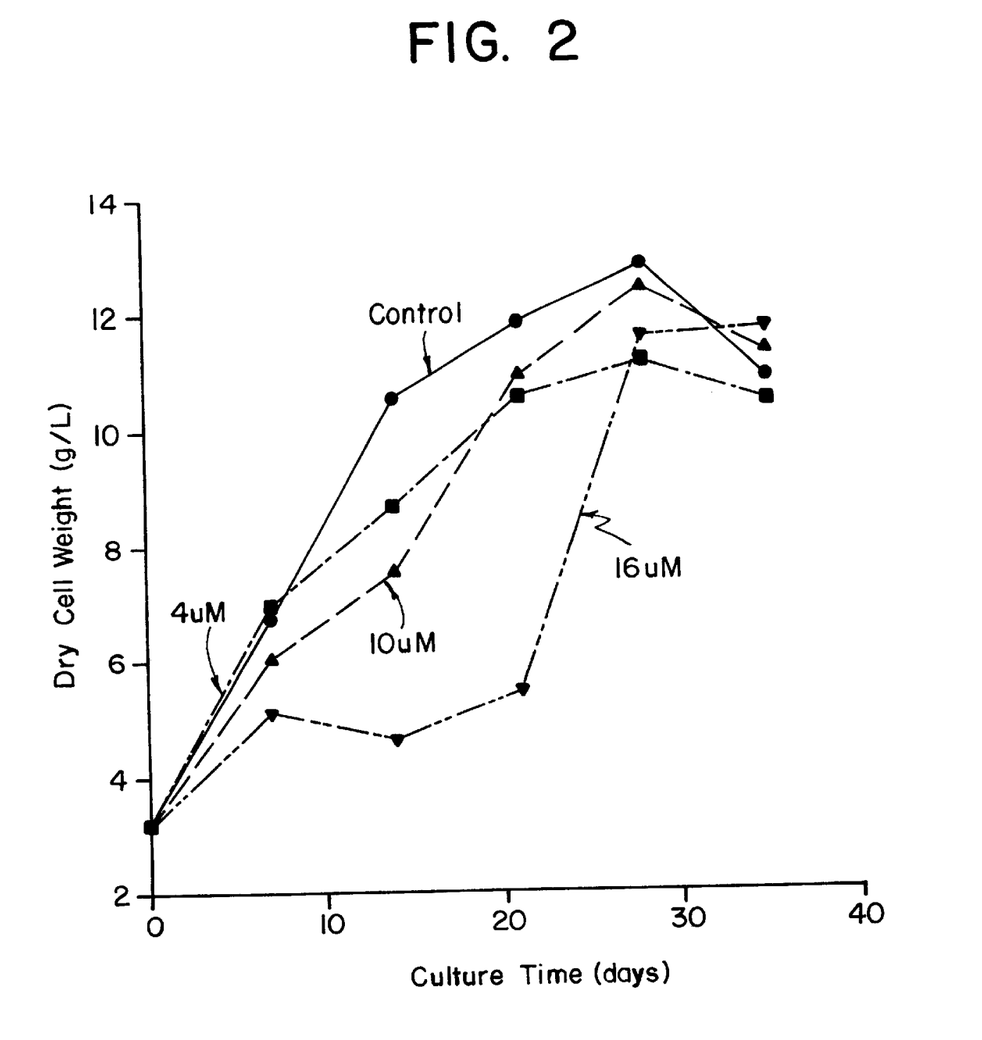
FIG. 2 is a graph showing the effect of $AgNO_3$ on the dry cell weight of Taxus genus plant cell.
Figure 3:
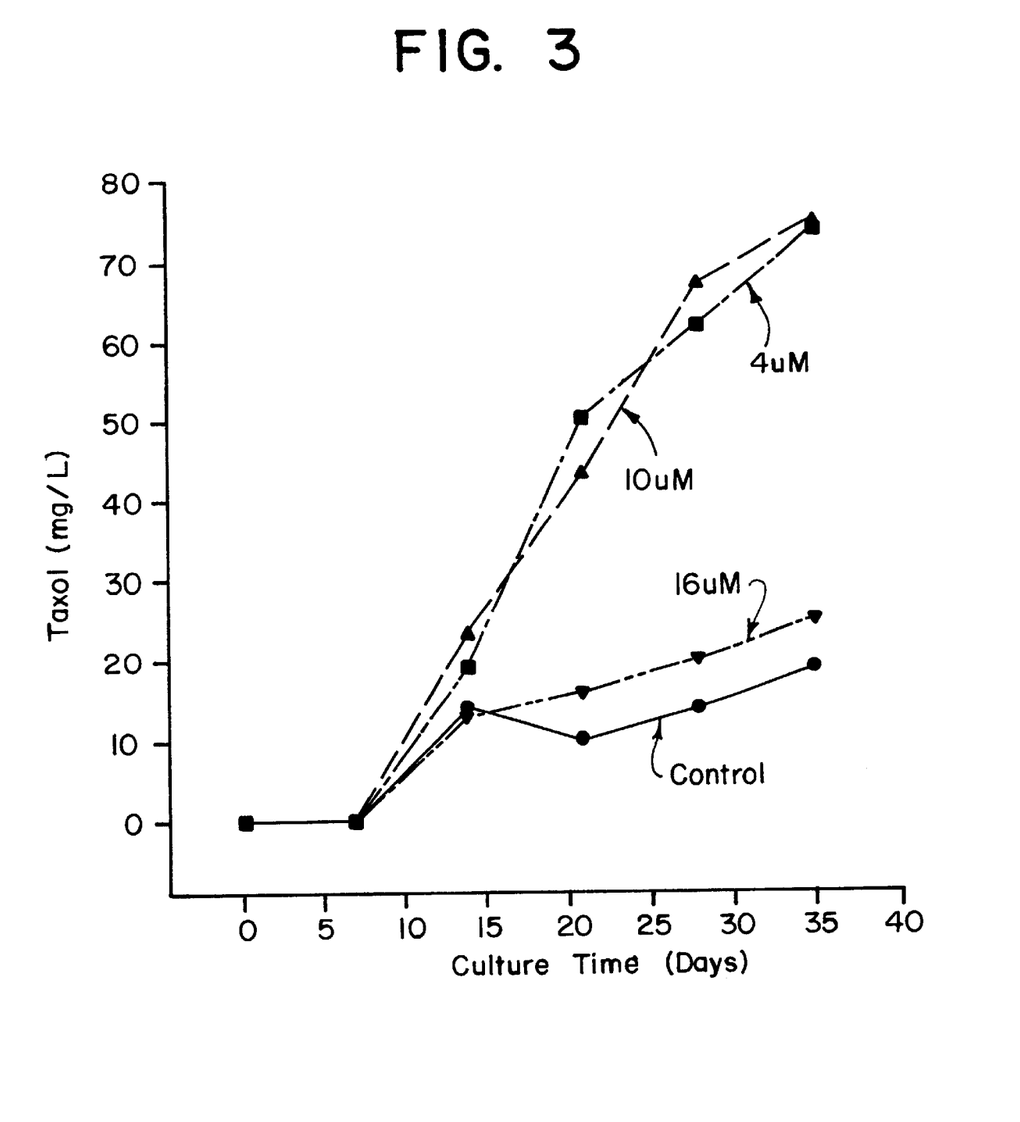
FIG. 3 is a graph showing the relationship of $AgNO_3$ concentration and taxol productivity.

SYG-1 was cultured analogously as in Example 3 except for varying AgNO₃ concentration of 0 $\mu$M, 4 $\mu$M, 10 $\mu$M, and 16 $\mu$M, respectively. And then, dry cell weight and taxol productivity depending on the AgNO₃ concentration were determined, respectively (see: FIGS. 2 and 3). As can be seen in FIGS. 2 and 3, it was strongly suggested that excess of AgNO₃ (>15 $\mu$M) inhibited normal growth of Taxus genus plant cell and, subsequently, taxol production. Under the consideration of the cytotoxic effect of high concentration of AgNO₃, it can be concluded that the concentration range from 1 to 15 $\mu$M is adequate for both active cell growth and efficient taxol production.

EXAMPLE 5
Effect of NH₄-Citrate on the Taxol Productivity

Figure 4:
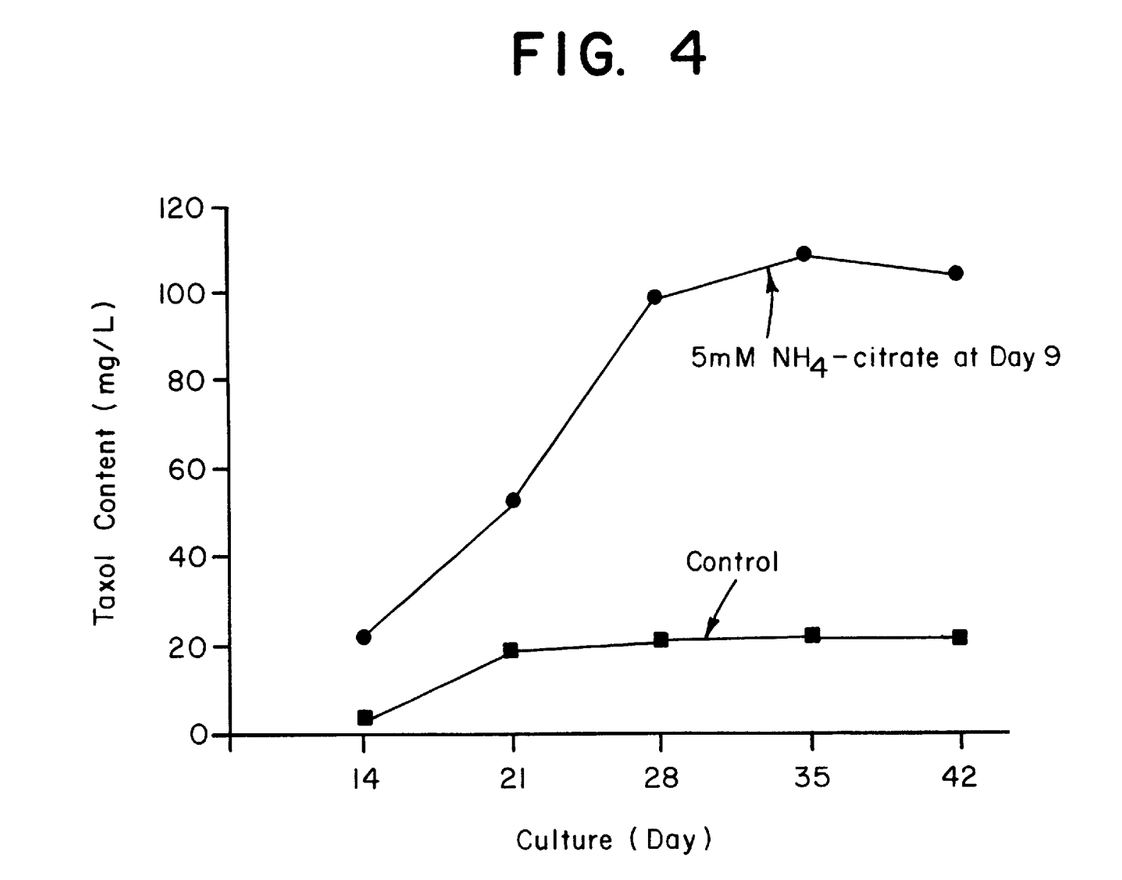
FIG. 4 is a graph showing the effect of $NH_4$-citrate on the taxol productivity.

The productivity of taxol in a suspension culture of SYG-1 was monitored, after the addition of NH₄-citrate. To a 250 ml of Erlenmeyer flask was poured 75 ml of B5 medium, and 14 day old cell culture was inoculated on this medium in a ratio of ~4 g (dry weight) per liter of medium and incubated under the same growth condition described in Example 2. Then, 5 mM of NH₄-citrate was added to the culture after 9 days of incubation, and the taxol productivity was compared with a control in which NH₄-citrate was not added (see: FIG. 4). As can be seen in FIG. 4, it was determined that the amount of taxol produced was about 103.6 mg/L when NH₄-citrate was added to a medium (-●-), which was 4.9 times the control (-○-).

EXAMPLE 6
Effect of Maltose on the Taxol Productivity

It has been well known that an increase of sugar concentration in a plant cell culture leads to an increase in secondary metabolite production. For example, it has been reported that: addition of 3% (w/v) sucrose and 5% (w/v) mannitol has improved the productivity of antocyanin in callus culture of Daucus carota (see: Knobloch, K.-H., et al., Zeiteshrift fur Natruforschung, 35c:55–556(1981)); and, 88 mM sucrose and 165 mM mannitol heightened the antocyanin productivity in a suspension culture of Vitis vinifera (see: Rajendran, L., et al., Biotechnology Letters, 14(8):707–712 (1992)). On the other hand, the decrease in the growth and secondary metabolite production were also reported when the amount of sugar over a certain concentration was added, possibly due to osmotic stress(see: Do, C. B. and Cormier, F., Plant Cell Reports, 9:500–504 (1990)).

Figure 5:
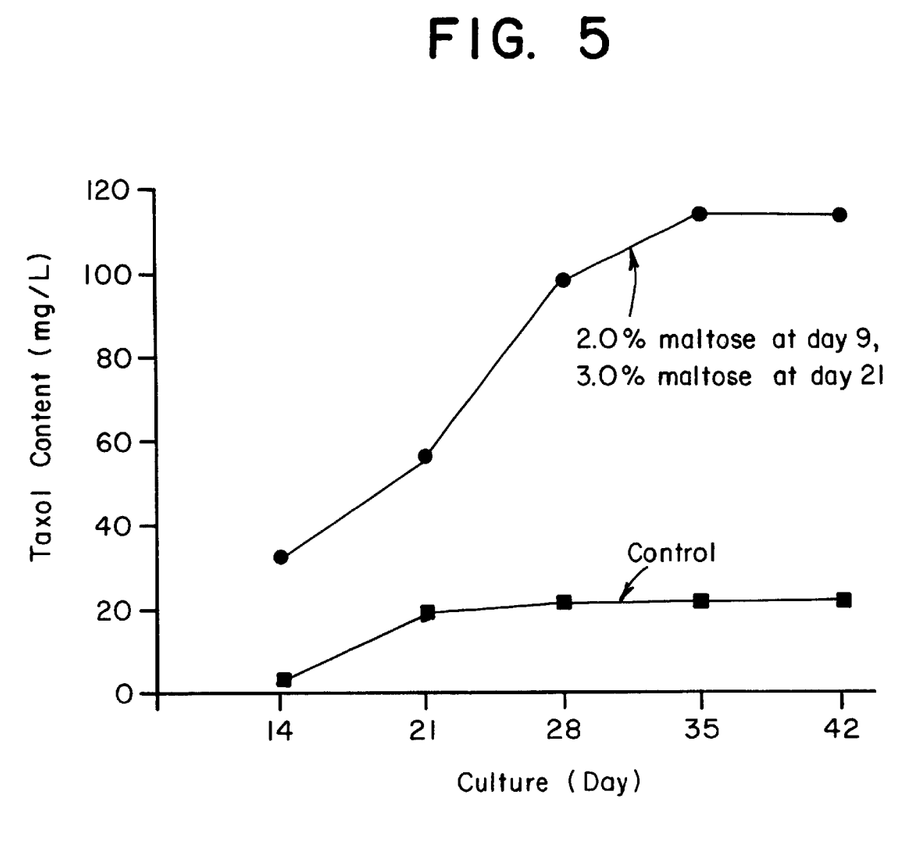
FIG. 5 is a graph showing the effect of maltose on the taxol productivity.

The effect of maltose addition to SYG-1 culture was evaluated. To a 250 ml of Erlenmeyer flask was poured 75 ml of B5 medium, and 14 day old cell culture was inoculated on this medium in a ratio of ~4 g (dry weight) per liter of medium and incubated under the same growth condition described in Example 2. Then, 2% (w/v) and 3% (w/v) of maltose were added to the culture after 9 days and 21 days of incubation, respectively, and the productivity of taxol was compared with a control which did not contain maltose (see: FIG. 5). As can be seen in FIG. 5, it was determined that the amount of taxol was 112.75 mg/L when maltose was added to a medium (-●-), which was 5.3 times the control (-○-).

EXAMPLE 7
Semi-Continuous Culture of Various Taxus Chinensis Cell Lines

Based on the results obtained in Examples 2 to 6, taxol was prepared by employing semi-continuous culture of Taxus chinensis SYG-1 ("SYG-1") and Taxus chinensis HU-1 ("HU-1").

Figure 6:
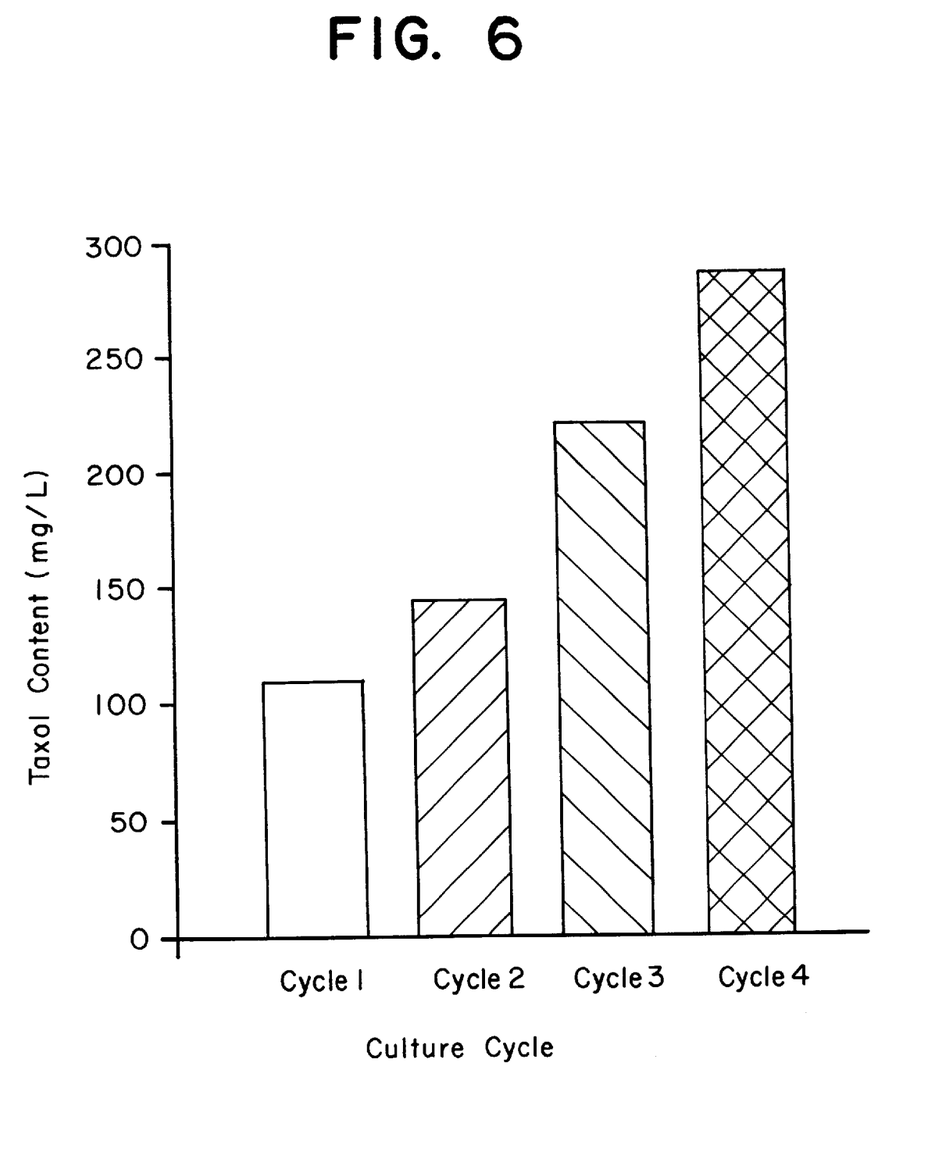
FIG. 6 is a graph showing the productivity of taxol in semi-continuous culture of SYG-1.

To a 250 ml of Erlenmeyer flask was added 80 ml of B5 medium and 14 day old SYG-1 or HU-1 culture was inoculated on the medium in a ratio of ~4 g (dry weight) per liter of medium for the final culture volume to be about 100 ml. Then, 10 $\mu$M AgNO₃ was added at the beginning of culture, followed by the addition of 5 mM NH₄-citrate and 2% (w/v) maltose after 9 days of incubation. After 21 days of incubation, 20 ml of culture equivalent to ⅕ volume of total culture was transferred to other flask containing 80 ml fresh medium to start another cycle of culture. Then, to 80 ml of remnant culture equivalent to ⅘ volume of total culture, was added 3% (w/v) maltose, and incubated for additional 21 days in which taxol production is maximized. At this time, incubation was made at 24° C., and an agitation speed of 150 rpm. Culture samples were taken periodically to check for microbial contamination, which showed no contamination. The amount of taxol produced in the culture was also determined by employing high performance liquid chromatography (HPLC, Waters, U.S.A.) as described above. As a result, it was found that taxol concentration was increased in accordance with the culture cycle in culture of both SYG-1 and HU-1, while the productivity of taxol after 4 cycles of cultivation of SYG-1 was determined to be 284 mg/L (see: FIG. 6 and Table 5).

TABLE 5

The productivity of taxol in semi-continuous culture of HU-1 (unit: mg/ml)

| Cycle | Taxol productivity |
|---|---|
| 1st | 0.9 |
| 2nd | 2.4 |
| 3rd | 6.8 |

EXAMPLE 8
Effect of Initial Concentration of Sugar on the Taxol Productivity

Figure 7:
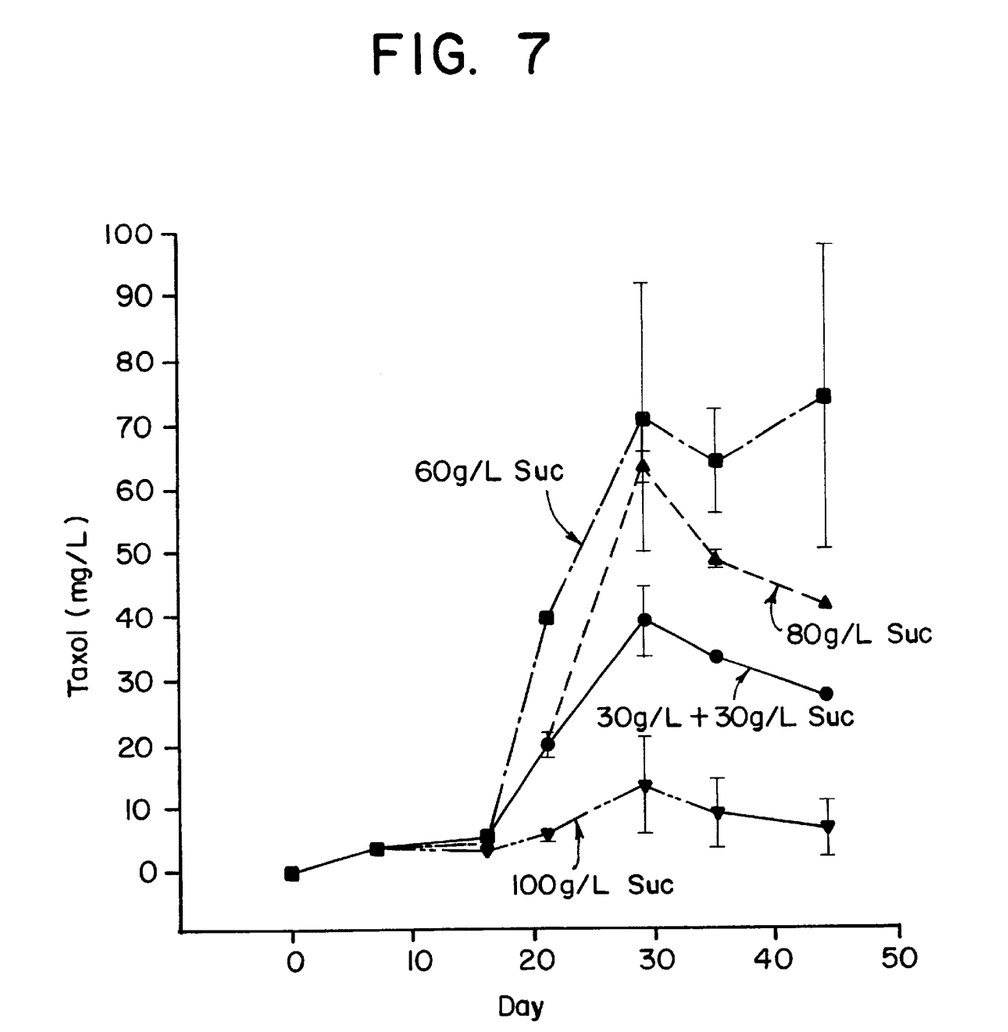
FIG. 7 is a graph showing the effect of initial concentration of sucrose on the taxol productivity.

To each of four 250 ml of Erlenmeyer flask was added 75 ml of B5 medium and 14 day old SYG-1 culture was inoculatd on the medium in a ratio of ~4 g (dry weight) per liter of medium. Then, 10 $\mu$M AgNO₃ and 0, 3, 5 or 7% (w/v) sucrose were added at the beginning of culture to adjust initial sugar concentration in the medium to 3, 6, 8 and 10% (w/v), respectively. After 14 days of incubation, only the culture which had been added no sucrose was added 3% (w/v) sucrose. At this time, incubation was made at 24° C., and an agitation speed of 150 rpm. The productivities of taxol in these cultures were monitored over about 45 days of incubation (see: FIG. 7). As can be seen in FIG. 7, it was determined that the addition of 3% (w/v) sucrose to culture medium at the beginning of culture (i.e., the initial sucrose concentration of 6% (w/v)) increased the amount of taxol produced after 30 day incubation to the level of 74.5 mg/L (-■-)

EXAMPLE 9
Effect of Initial Concentration of Cell on the Taxol Productivity

Figure 8:
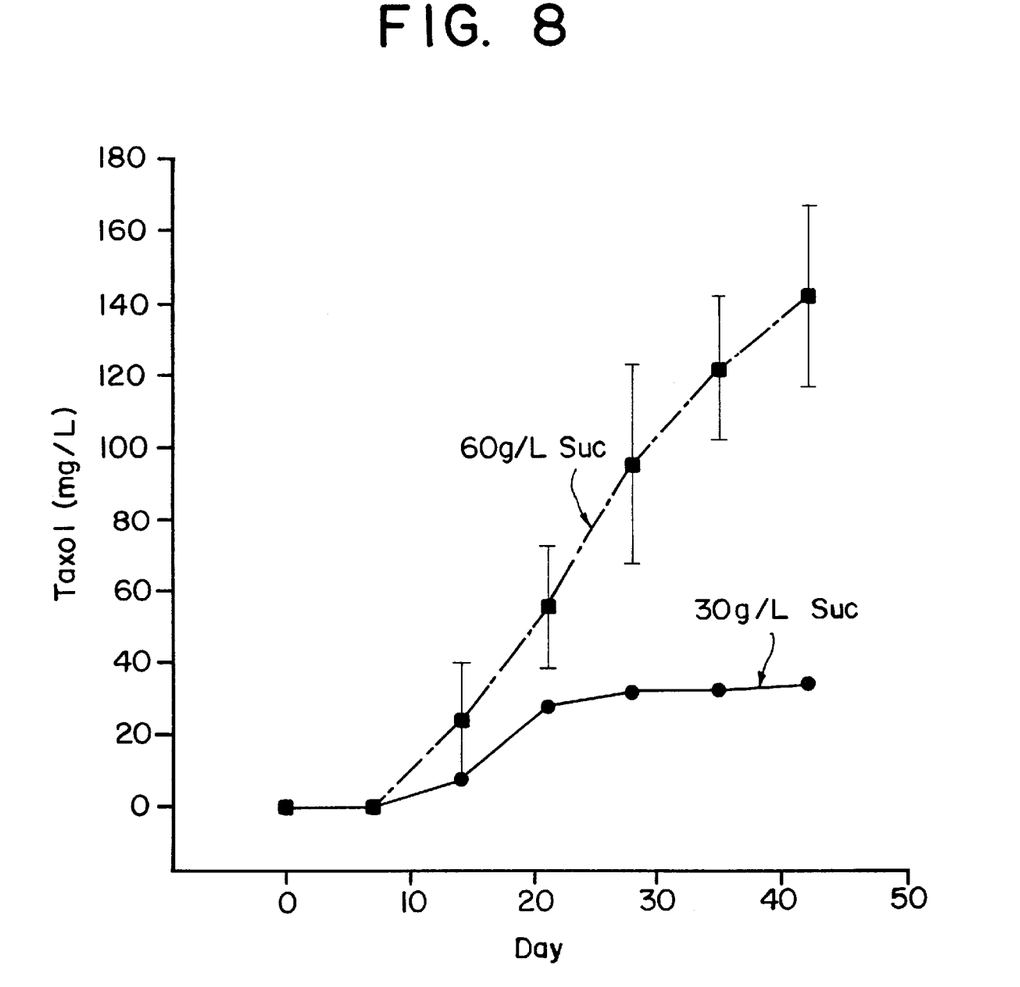
FIG. 8 is a graph showing the effect of initial concentration of Taxus genus plant cell on the taxol productivity.

To a 250 ml of Erlenmeyer flask was added 50 ml of B5 medium and 14 day old SYG-1 culture was inoculated on the medium in a ratio of ~8 g (dry weight) per liter of medium. Then, 4 $\mu$M AgNO$_3$ and 0 or 3% (w/v) sucrose were added at the beginning of culture. The productivities of taxol in these cultures were monitored over about 45 days of incubation (see: FIG. 8). As can be seen in FIG. 8, compared to FIG. 7, it was determined that higher initial concentration of cell increased the amount of taxol produced.

As clearly illustrated and demonstrated as aboves, the present invention provides a method for mass production of taxol which comprises adding sugar into a culture medium containing sugar in the course of semi-continuous culture of Taxus genus plant cell, and a universal method for mass production of taxol which comprises culturing Taxus genus plant cell in a culture medium containing sugar and AgNO$_3$ as well. In accordance with the present invention, large amount of taxol can be produced with a high yield, simply by manipulating the culture condition of Taxus genus plant cell culture.

What is claimed is:

1. A method for mass production of taxol by semicontinuous culture of Taxus genus plant cell, which comprises the steps of:
    (i) inoculating Taxus genus plant cells on a culture medium containing 1 to 10% (w/v) sugar and 1 to 15 $\mu$M AgNO$_3$, and incubating said cells;
    (ii) adding 1 to 15 mM NH$_4$-citrate and 1 to 10% (w/v) sugar after between 5 and 20 days of incubation at step (i);
    (iii) transferring a part of the culture solution containing the Taxus genus plant cells obtained in step (ii) to fresh medium for a volume ratio of said culture solution to said fresh medium to be in the range of 1/10 to 1/2 and repeating incubation steps (i) and (ii);
    (iv) adding sugar to the solution remaining after transfer of the solution from step (iii) at a concentration of 1 to 10% (w/v) and incubating said cells; and,
    (v) recovering taxol from the culture solution in which said taxol is produced by said cells.

2. The method of claim 1, wherein the Taxus genus plant is selected from the group consisting of *Taxus brevifolia, Taxus canadensis, Taxus cuspidata, Taxus baccata, Taxus globosa, Taxus floridana, Taxus wallichiana, Taxus media* and *Taxus chinensis*.

3. The method of claim 1, wherein the Taxus genus plant is *Taxus chinensis* or *Taxus baccata*.

4. The method of claim 1, wherein the plant cells are inoculated on the culture medium in a ratio of 4 to 8 g (dry weight) per liter of medium.

5. The method of claim 1, wherein the culture medium contains 4 to 9% (w/v) sugar.

6. The method of claim 1, wherein the sugar is one or two selected from the group consisting of glucose, fructose, sucrose, and maltose.

7. A method for mass production of taxol by culture of Taxus genus plant cell, which comprises the steps of:
    (i) inoculating Taxus genus plant cells on a culture medium containing 1 to 10% (w/v) sugar and 1 to 15 $\mu$M AgNO$_3$, and incubating said cells;
    (ii) adding 1 to 15 mM NH$_4$-citrate and 1 to 10% (w/v) sugar after between 5 and 20 days of incubation at step (i); and
    (iii) recovering taxol from the culture solution in which said taxol is produced by said cells.

8. The method of claim 7, wherein the culture of Taxus genus plant cell includes continuous culture, semi-continuous culture, batch culture and fed-batch culture.

9. The method of claim 7, wherein the Taxus genus plant is selected from the group consisting of *Taxus brevifolia, Taxus canadensis, Taxus cuspidata, Taxus baccata, Taxus globosa, Taxus floridana, Taxus wallichiana, Taxus media* and *Taxus chinensis*.

10. The method of claim 7, wherein the Taxus genus plant is *Taxus chinensis* or *Taxus baccata*.

11. The method of claim 7, wherein the Taxus genus plant cell is *Taxus chinensis* SYG-1(KCTC 0232BP).

12. The method of claim 7, wherein the plant cells are inoculated on the culture medium in a ratio of 4 to 8 g (dry weight) per liter of medium.

13. The method of claim 7, wherein the culture medium contains 4 to 9% (w/v) sugar.

14. The method of claim 7 wherein the sugar is one or two selected from the group consisting of glucose, fructose, sucrose and maltose.

* * * * *